United States Patent [19]

Smith et al.

[11] Patent Number: 4,596,558
[45] Date of Patent: Jun. 24, 1986

[54] PULSED EXTERNAL MEDICATION DISPENSER

[75] Inventors: Timothy J. N. Smith; Alois J. van Eyken, both of Kingston, Canada

[73] Assignee: Queen's University at Kingston, Kingston, Canada

[21] Appl. No.: 775,997

[22] Filed: Sep. 13, 1985

[51] Int. Cl.$^4$ .............................................. A61M 5/00
[52] U.S. Cl. ..................................... 604/134; 604/142; 604/246; 604/249; 128/DIG. 12; 222/61
[58] Field of Search ................. 604/142, 104, 131, 33, 604/132, 245, 246, 249; 128/DIG. 12, DIG. 13; 222/61, 504

[56] References Cited

U.S. PATENT DOCUMENTS

| | | | |
|---|---|---|---|
| 3,640,277 | 2/1972 | Adelberg | 222/61 X |
| 3,734,351 | 5/1973 | Gaudin | 604/134 X |
| 3,923,060 | 12/1975 | Ellinwood, Jr. | 128/DIG. 13 X |
| 4,038,981 | 8/1977 | Le Fevre et al. | 604/65 |
| 4,227,724 | 5/1982 | Birk et al. | 604/67 |

Primary Examiner—Stephen C. Pellegrino
Attorney, Agent, or Firm—Richard J. Hicks

[57] ABSTRACT

A pulsed liquid injection device for injection of predetermined doses of medication at predetermined intervals of time is described. A bag containing medication is maintained under pressure and is connectable via a three way valve, operable by means of an electronic timing device, to a second pressurized metering container which is smaller than the bag containing the medication. The pressure in the bag is higher than that of the metering device and the metering container is always at a pressure required for injection. The timing device operates the valve at intervals to (a) charge the metering container from the bag and (b) inject the charge in the metering container into the patient. The valve includes a blanking device to eliminate the possibility of injecting the patient directly from the bag.

18 Claims, 14 Drawing Figures

PULSED EXTERNAL MEDICATION DISPENSER

FIELD OF INVENTION

The present invention relates to a pulsed liquid injection device primarily developed for the injection of liquid in predetermined doses at predetermined intervals into a living organism, especially a female human being. However, the invention may be applied to the injection of liquid in predetermined doses at predetermined intervals into non-living systems for purposes of fabrication, lubrication, adding paint additives, food processing or the carrying out of precise chemical reactions.

DESCRIPTION OF THE PRIOR ART

It is known to apply spring pressure to the walls of a flexible bag in order to pressure the liquid therein for its supply to a point of use. Thus U.S. Pat. No. 1,102,953, M. J. RABAT, issued July 7, 1914 and U.S. Pat. No. 3,780,732, S. LEIBINSOH issued Dec. 25, 1973 relate to such devices.

U.S. Pat. No. 4,327,724, M. Birk, issued May 4, 1982 discloses an injection device operated by a piston-type motor driven by an external source of compressed air. The motor piston can pull the piston of a normal single use syringe to draw liquid into the syringe through a 3 way cock from a liquid reservoir. The 3 way cock is then repositioned by a second piston-type motor to connect the syringe to a catheter, while isolating the reservoir. The first motor piston then pushes the piston of the injection syringe to discharge a measured quantity of the liquid through the 3 way cock towards the catheter and thus the patient.

OBJECT OF THE INVENTION

For certain purposes, for example the correct dosing of a female patient with fertility-improving drugs, it is necessary to inject, either subcutaneously or intravenously, predetermined doses of a liquid at predetermined intervals. Up to now, this has necessitated the use of bulky equipment which is both expensive and fragile, unless of course the injections are carried out manually. Furthermore, because of the power requirements of known devices, it is not possible for a patient to wear them in an inconspicuous manner. An object of the present invention is thus the provision of a pulsed liquid injection device which is inherently small, light, relatively cheap and has very small power requirements. A further objective is the provision of means by which the medication in such a device can be replaced simply and easily with very little risk of the introduction of infection.

SUMMARY OF THE INVENTION

According to one aspect of the present invention, a pulsed liquid injection device comprises a first liquid storage container adapted to store liquid under pressure greater than that required for making injections, a second liquid metering container also adapted to store liquid under a pressure greater than that required for making injections and having a predetermined capacity for liquid at the pressure in the first container at all times, valve means having first, second and third ports and having a first operating condition in which the valve means connect together the first and second ports but blank off the third port, and a second operating condition in which the valve means blank off the first port but connect together the second and third ports, first liquid flow passages connecting the first port to the interior of the first storage container, second fluid flow passages connecting the second port to the interior of the second metering container, a liquid dispensing duct connected to said third port and electrical timing means arranged repeatedly at predetermined intervals to apply an electrical operating pulse to the said valve means to change them from one initial operating condition to the other and, after a delay determined by the pulse length, to permit the valve means to return to their initial position.

According to another aspect of the invention, a cassette adapted for addition to a pulsed liquid injection system, of which it then forms part, the cassette including in its package a first liquid storage container adapted to store liquid under pressure greater than that required for making injections, a second liquid metering container also adapted to store said liquid under a pressure greater than that required for making injections and having a predetermined capacity for liquid at the pressure in the first container, valve means having first, second and third ports and having a first operating condition in which the valve means connect together the first and second ports but blank off the third port, and a second operating condition in which the valve means blank off the first port but connect together the second and third ports, first liquid flow passages connecting the first port to the interior of the first storage container, second fluid flow passages connecting the second port to the interior of the second metering container, a liquid dispensing duct connected to said third port, and electrical operating means for the valve means adapted upon application of an electrical pulse to change the valve means from one initial operating condition to the other and, after a delay determined by the pulse length, to permit the valve means to return to their initial position.

BRIEF EXPLANATION OF THE DRAWINGS

The invention will now be described, by way of example, with reference to the accompanying drawings, in which.

DETAILED DESCRIPTION OF THE FIRST EMBODIMENT OF THE INVENTION

Figure 1:
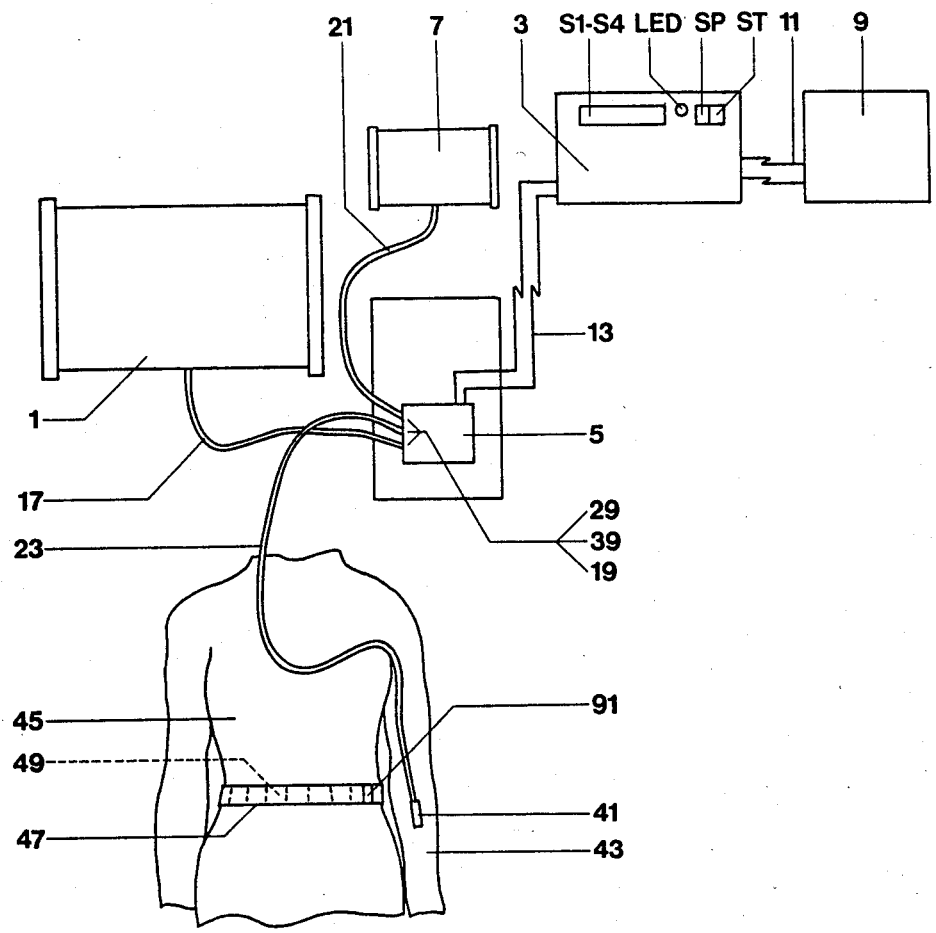
FIG. 1 is a schematic diagram of the parts of a device for pulsed liquid injection; the various parts shown are not drawn to the same scale; this figure relates to a first embodiment of the invention.

Referring first to FIG. 1, this is a schematic diagram, not drawn to scale, of the parts of a device for the pulsed injection of a liquid into a female patient. The patient in this specific example suffers from a hormone imbalance and the object is to inject specific doses of the liquid at specific intervals. The device includes a first liquid storage container 1, adapted for the storage of the liquid to be injected under a pressure greater than that needed to effect the injection. Further, an electrical pulse generator and timer 3, a three port valve device 5, and a second liquid measuring or metering container 7. An electrical battery 9 is connected by flexible leads 11 to the pulse generator and timer 3, and the output from timer 3 is applied through flexible leads 13 to the valve device 5. A first small bore flexible pipe 17 connects the interior of the first container 1 to a first port 19 of the valve device 5. A second small bore flexible pipe 21 connects the interior of the second container 7 to a second port 29 of the valve device 5. A third small bore flexible pipe 23 connects the third port 39 of the valve device 5 to a catheter 41 shown inserted into the lower arm 43 of a female patient 45. The patient 45 is shown as wearing a belt 47 which is formed with pockets 49 into which the various items shown and described above are fitted, with of course the exception of the pipe 23, which serves as a liquid discharge tube.

Figure 2:
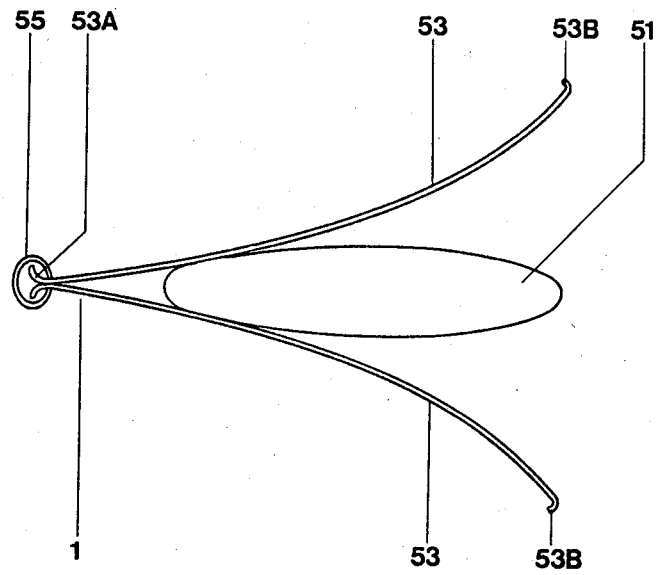
FIG. 2 is a side view of the main parts of a liquid storage container shown in FIG. 1, before assembly.
Figure 3:
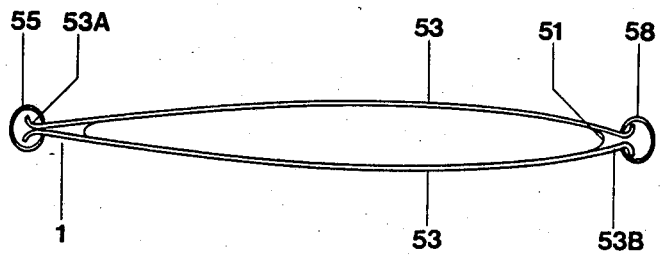
FIG. 3 is a side view of that storage container, after assembly.

FIG. 2 illustrates the construction of the first liquid storage container 1, while FIG. 3 illustrates the operative state of the container. A flexible bag 51 formed of thin polyethylene sheeting and having flexible walls is disposed between two precurved spring metal leaf springs 53. FIG. 2 shows the initial shapes of the springs 53, which are held together along one end 53A by a C-section channel 55. The bag 51, containing the desired liquid, is positioned between springs 53, which are then forced together to the position shown in FIG. 3 and a second C-section channel 58 applied along the second end 53B. The liquid in the bag is thus pressurized, in the example shown to about 10 pounds per square inch.

Figure 4:
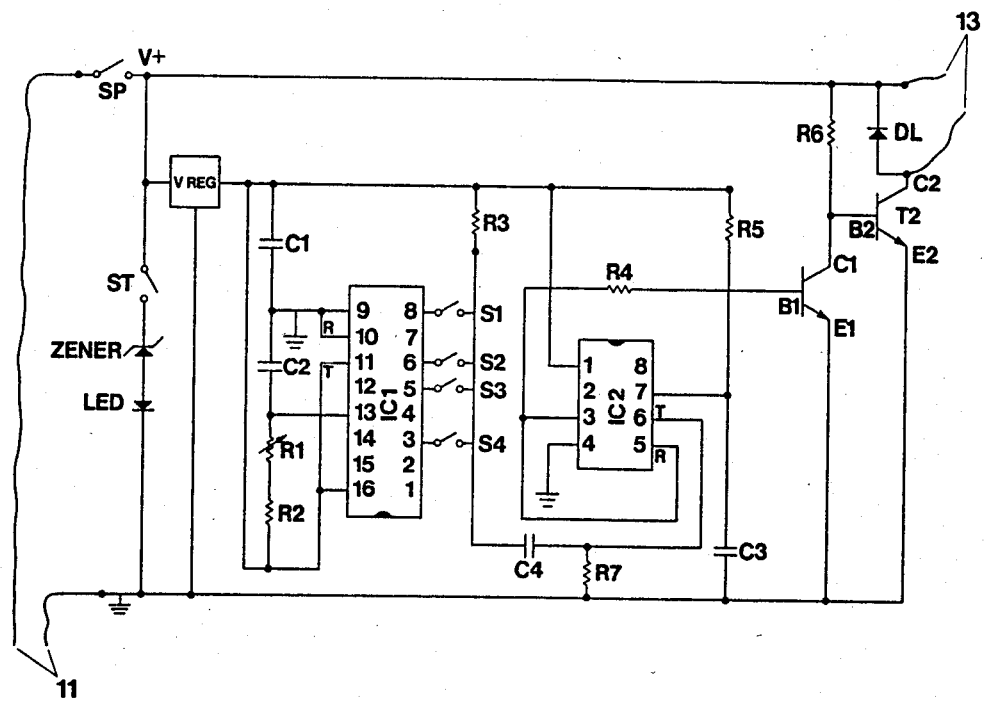
FIG. 4 is a circuit diagram of an electrical pulse generator and timer.

FIG. 4 is a circuit diagram of the electrical pulse generator and timer 3. For the sake of completeness, the particulars of the various circuit components are listed below:

| Component | Description |
|---|---|
| IC1 | ICM7240IJE - CMOS Programmable Counter/Timer |
| IC2 | ICM7242IJA - CMOS Long Range Counter/Timer |
| T1 | F2N3904 - switching transistor |
| T2 | M2N6426 - Darlington transistor |
| R1 | 1 megohm multi-turn trim potentiometer |
| R2 | 680K · ohms resistor |
| R3 | 820K · ohms resistor |
| R4 | 2.2 M · ohm resistor |
| R5 | 390K · ohms resistor |
| R6 | 820K · ohms resistor |
| R7 | 820K · ohms resistor |
| C1 | 68 F capacitor |
| C2 | 68 F capacitor |
| C3 | 104 nF capacitor |
| C4 | 104 nF capacitor |
| VREG | NSC LM 29312 - 5.0 - 5.0 volt voltage regulator |
| DL | 1 N 914 B - back emf release |
| ZENER | 1 N 4739 A - Zener diode - 9.1 volt |
| LED | NSL4944 - constant current light emitting diode |
| SP | main power switch |
| ST | battery level test switch |
| S1 | 8 hour dosage interval control switch |
| S2 | 3 hour dosage interval control switch |
| S3 | 1 hour dosage interval control switch |
| S4 | 15 minute dosage interval control switch |

Figure 5:
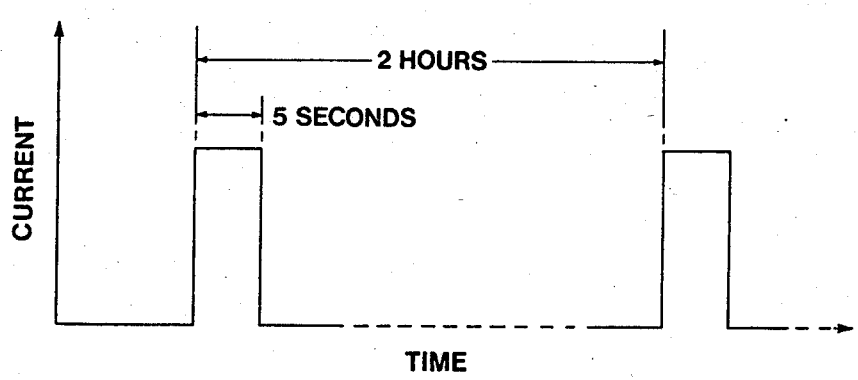
FIG. 5 is a diagram of pulses produced by the timer of FIG. 4.

It will be seen that the battery leads 11 are applied to the left-hand side of this circuit, while the leads 13 from the timer 3 to the valve device 5 extend from the upper right-hand side of the circuit. As will be appreciated by those skilled in the electrical/electronic arts, this electrical circuit is basically a clock device, the frequency of which can be varied by adjustment of R1, the multi-turn trim potentiometer. Associated with the clock device is a counter which will provide an output according to a count determined by the setting of the switches S1 through S4. Only one of these switches should be closed, and in the example shown R1, the multi-turn trim potentiometer, is set to enable selection of one of the periods 8 hours, 2 hours, 1 hour and 15 minutes. At the predetermined clock count, the circuit will produce a step-type electrical output pulse. In the example shown, one of the switches S1 through S4 (shown open) was actually set to produce an electrical pulse every 2 hours. The duration of the pulses so produced has been arbitrarily set for 5 seconds for reasons which will be discussed below. FIG. 5 is a diagram showing two such pulses of current produced in leads 13 to operate the valve device 5. In each case the pulse width is 5 seconds, and the interval b between onset of pulses is 2 hours.

Figure 6:
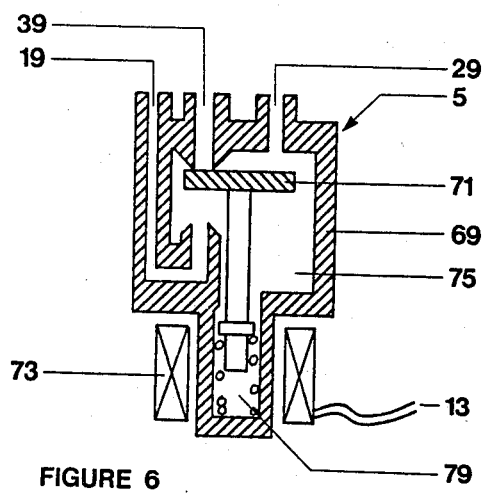
FIG. 6 is a sectional side elevation of a valve device, shown in a first operating position.
Figure 7:
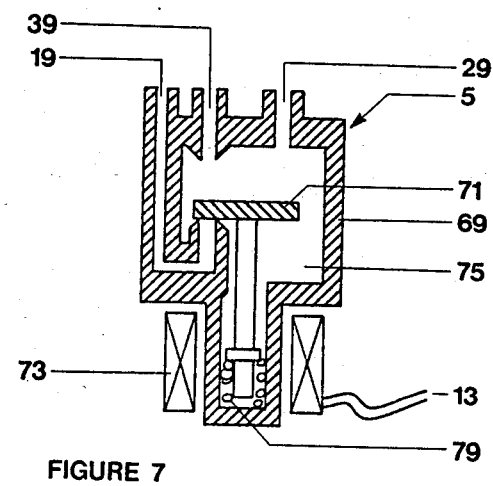
FIG. 7 is a similar side elevation, but showing the valve device in a second operating position.

FIGS. 6 and 7 illustrate diagrammatically the form and the operation of the valve device 5, which is a commercially available three-port shuttle valve. A valve of this general type is available commercially from Lee Manufacturing Company, 2, Pettipaug Road, Westbrook, Conn. 06498, U.S.A. as their model LFAA1Z01618H. Valve device 5 has a cylindrical body 69 in which is arranged an axially slidable shuttle 71 movable, by an electrical pulse applied along leads 13 to its solenoid operating coil 73 from the first operating position shown in FIG. 6 to the second operating position shown in FIG. 7. In the first position (FIG. 6) the solenoid coil 73 is de-energized, valve ports 19 and 29 are connected together through a chamber 75 in the valve body 69. At the same time, valve port 39 is blocked off by shuttle 71. In this absence of a suitable applied electric pulse to the solenoid coil 73, a coil spring 709 acting between the shuttle 71 is in the position shown in FIG. 6, and holds it in that position. An electrical pulse input along leads 13 to solenoid 73 will overcome the opposing force of the coil spring 79 and drive the shuttle 71 to the second operating position of the valve device 5 shown in FIG. 7, in which chamber 75 connects together valve ports 29 and 39, while valve port 19 is blocked off by shuttle 71.

Figure 8:
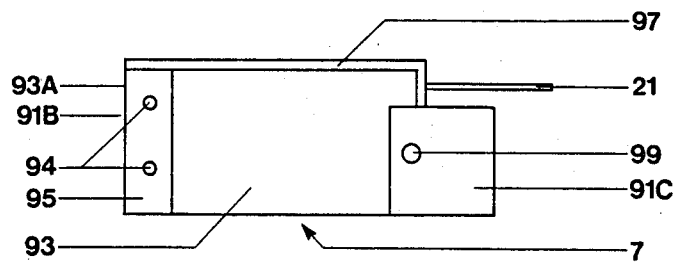
FIG. 8 is a plan view of a second liquid metering container.
Figure 9:
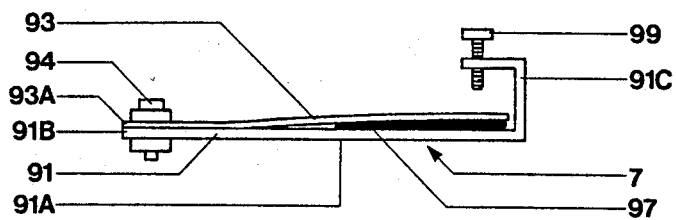
FIG. 9 is a side elevation of the container shown in FIG. 8, in an uncharged condition.
Figure 10:
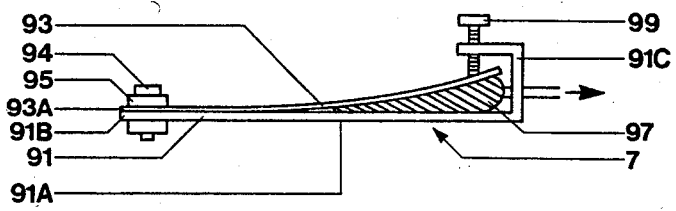
FIG. 10 is a side elevation of the device of FIG. 8, in a fully charged condition.

FIGS. 8, 9 and 10 illustrate the second metering container 7. This container is arranged to store the liquid at all times under a pressure greater than that required for injections, but furthermore is arranged to accept only a limited amount of the liquid when the liquid is supplied at the pressure in the first chamber. A rigid plate 91 is formed as shown in these Figures to provide a flat part 91A extending from one end 91B and continued as an upwardly curved portion. A leaf spring 93 is clamped along one end 93A to end 91B of plate 91 by two bolts 94 which extend through metal clamp plates 95 and both plate 91 and spring 93. The leaf spring 93 is initially prestressed so that, in the absence of fluid in bag 97, the leaves 93, 91A lie in impressed juxtaposition to each other as shown in FIG. 9. The flexible bag 97 forming the actual container 7 is positioned between plate 91 and leaf spring 93. As liquid is forced into this bag 97, it deflects the leaf spring 93 upwardly. This upward movement is limited by an adjustable stop screw 99 mounted in part 91C of plate 91, (see FIG. 10). The setting of the screw 99 will determine how much liquid can be forced into the bag 97 by the pressure in container 1. It is of course necessary that the spring 93 is soft enough to permit flexing as described, while being stiff enough to create in bag 97 a pressure in excess of that required for making injections.

Figure 11:
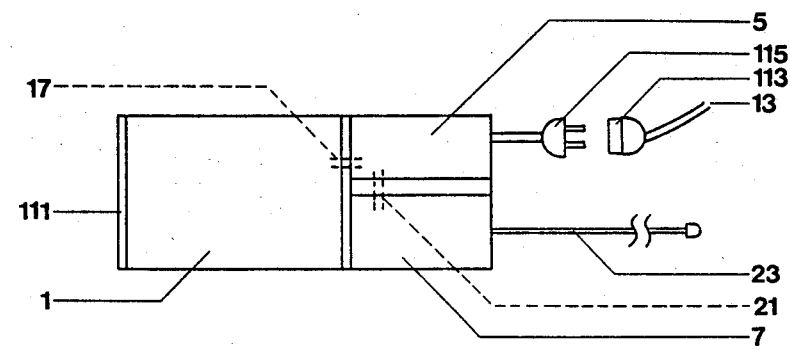
FIG. 11 is a front view of a disposable cassette.

FIG. 11 depicts a disposable cassette 111 in which are mounted the first liquid storage container 1, the second liquid metering container 7, the valve means 5 and the pipes 17 and 21. Pipe 23 extends out of the cassette. The leads 13 terminate in a female socket 113 and the cassette is provided with a complementary plug 115.

Figure 12:
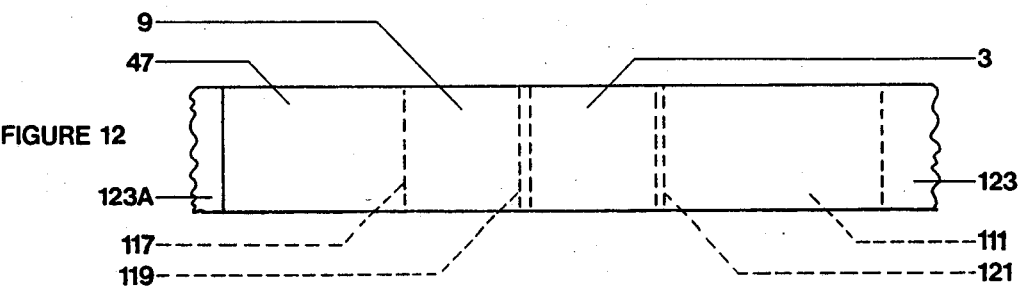
FIG. 12 is a front view of a belt shown in FIG. 1.

FIG. 12 illustrates part of the belt 47, and shows three pockets 117, 119 and 121 which accommodate respectively the battery 9, the timer 3 and the cassette 111. The belt is formed of a canvas-type material with a soft inner lining, and is secured in place by a securing device 123, 123a, such as the two-part securing material known as VELCRO (trade mark).

OPERATION AND USE OF FIRST EMBODIMENT

The particular medical problem which led to the present invention was that some 10% of North American couples suffer from infertility. This has created a major impetus for the development of new methods to regulate the reproductive function. One such project involves the intermittent (pulsatile) administration of gonadotropin releasing hormone to the female patient, either intravenously or subcutaneously. It was found that the brain normally releases this hormone in discreet pulses at intervals of about 2 hours. Further that unless the pattern of injections used by the brain is copied, the reproductive process is not suitably stimulated. Further, the injections may have to be continued for several weeks for reproduction to be obtained.

Since it is hardly practical for the patient to ensure the manual injection of the medication typically every two hours, some form of automatic injection machine was required. However, existing pulsatile machines used in general medicine are expensive, complicated and so bulky as to render onerous their supply to and carrying by a female patient for several weeks.

In use of the apparatus described and illustrated, initially the first liquid storage container 1 is filled with the desired medication under a pressure of 10 pounds per square inch. This pressure is considerably higher than the pressure in the human body for purposes of intravenous injections, which may be considered as about 3 pounds per square inch. Since valve device 5 initially is in the first operating position shown in FIG. 6 (the power supply switch SP being "off"), the overflow of liquid from valve chamber 75 through port 39 is blocked by the shuttle 71. The liquid discharge tube 23 is primed by closure of the "on/off" switch SP on timer 3. This causes the generation of an electrical pulse having a duration of five seconds, which is applied through leads 13 to the valve operating solenoid coil 73. This causes the shuttle 71 to move from the first operating position shown in FIG. 6 to the second operating position shown in FIG. 7, and to be held there for a period of five seconds. Liquid from the second liquid metering container 7 is free, during this 5 second period, to flow through pipe 21, valve port 29 through chamber 75 in the valve body 69 to the third valve port 39 and then out through pipe 23, which is thus purged of air. The period of five seconds is purposely chosen as being far in excess of the time needed for liquid at about 7 pounds per square inch in metering container 7 to flow through pipe 23 and the catheter 41 into the patient. The amount of liquid transferred by each pulse to the patient is dependent on the characteristics of the metering container 7 and the setting of the stop screw 99.

At the end of the five second period, the electrical pulse ends, and the valve shuttle 71 is brought back to the first operating position, that shown in FIG. 6, by the spring 79. Liquid is now free to flow from the storage container 1 through pipe 17 to valve port 19, through the chamber 75 in the valve body 69 to the port 29, and then through pipe 21 into the second metering container 7. Bag 97 inflates until inflation is stopped by engagement of the leaf spring 93 with stop screw 99. The system is now purged of air, and again outflow from storage container 1 is blocked by the shuttle 71 of the valve device 5. The power switch PS is then switched off and the various parts of the apparatus are fitted into the pockets 49 of the belt 47, which is fitted to the waist of the female patient 45. Pipe 23 is secured by medical tape to run up the body of the patient, down the inward side of the arm 43, and is inserted into the catheter 41. The apparatus is now ready for use.

USE OF THE DEVICE

The present invention is not directed to the medical problem of infertility, but to the provision of a pulsed liquid injection device capable of use as required by medical specialists. The timing, dosage, period of use and day/night continuity of use are all subjects of ongoing medical research. The present device can be set to accommodate variations found medically necessary. The following description therefore relates to proposed use of the device, but changes may be required for medical reasons.

Initially a patient will be supplied with the belt 47, the electrical timer 3 and a battery, which may be either disposable or rechargable. The patient is then supplied with a medication kit, which comprises the medication storage container 1, the metering container 7, the valve device 5, and the associated pipes 17, 21 and 23. These will be supplied as a complete unit, and preferably will be combined as indicated in a cassette. The free end of the pipe 23 will preferably be sealed with a readily removable cap, and the cassette enclosed in a sealed sterile package.

The patient will remove the cassette from its package, check that the battery is connected to the timer and that switch SP is "off". She then inserts plug 115 into socket 113 of the timer 3 and inserts the cassette into the appropriate pocket on the belt 47. The patient then selects, by setting one of the switches S1 through S4, a dosage interval as directed by her physician. After removal of the sealing cap from the free end of pipe 23, she closes the switch SP.

As described above, this causes the immediate generation of an electrical pulse, which purges tube 23 of air. The free end of pipe 23 is then connected to the catheter 41, and if the catheter is not currently inserted in the arm, a second dosage pulse will be required to purge the catheter of air before insertion, then the belt is comfortably fitted about the waist of the patient.

The device will now operate automatically and continuously until switch SP is switched "off". Some precautions are necessary; periodically the switch ST should be closed and diode LED observed to light to ensure that battery power is present; during sleep the belt can be removed and placed on a bedside table, the pipe 23 remaining attached to the catheter 41; and similarly, when the patient takes a shower, the belt and the parts of the device (apart from the catheter and the end of pipe 23) placed somewhere nearby which remains dry.

Suitably the cassette will bear an indication of the length of time for which it will provide medication, and when that time has expired the patient can readily disconnect the pipe 23 from the catheter and the plug 111 from the socket 115, and replace the cassette with a new one, in the manner described above.

From a medical point of view, it is anticipated that the patient will visit her physician regularly for ultrasound tests which will detect the maturity of a follicle in the ovary. Presence of a mature follicle leads to the probability of fertilization within the subsequent two days.

DETAILED DESCRIPTION OF THE SECOND EMBODIMENT OF THE INVENTION

Figure 13:
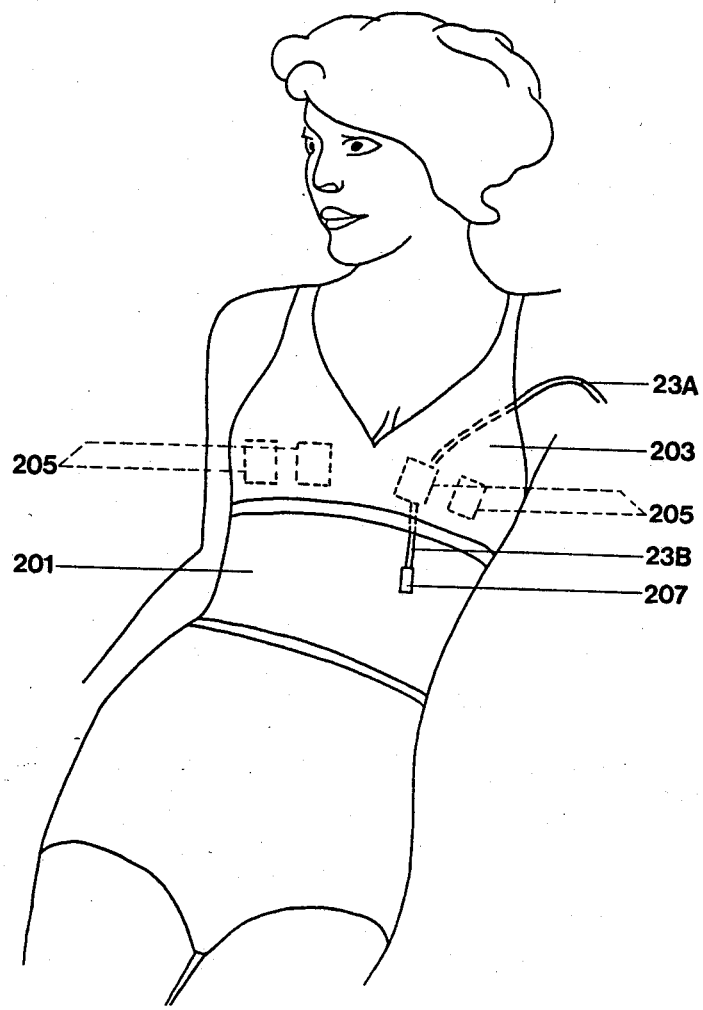
FIG. 13 is a pictorial view of a patient wearing a second embodiment of the invention.

FIG. 13 discloses a modification of the device shown in FIGS. 1 through 12. Firstly, the injection of the medication is made subcutaneously, and secondly, the parts of the device are carried in the brassiere of the patient. The description of FIGS. 1 through 12 applies to this embodiment, except that the female patient 201 is wearing a brassiere formed with pockets 205 in which the various parts of the device are carried and concealed. To this end, the patient wears a brassiere having a cup size larger than she would normally wear, and this provides sufficient room in the two cups to accommodate the necessary parts. By the addition of appropriate padding, the only apparent change is an increase in the bust size.

In FIG. 13 two possible configurations for the liquid dispensing pipe 23 are shown. Thus pipe 23A extends upwardly from the brassiere and, if used, would be connected to a catheter in the arm of the patient, as in FIG. 1. The alternative pipe 23B extends downwardly from the brassiere and is connected to a suitable subcutaneous injection needle 207.

The use and operation of the device of FIG. 13 is similar to that of the device of FIGS. 1 through 12.

DETAILED DESCRIPTION OF THE THIRD EMBODIMENT OF THE INVENTION

Figure 14:
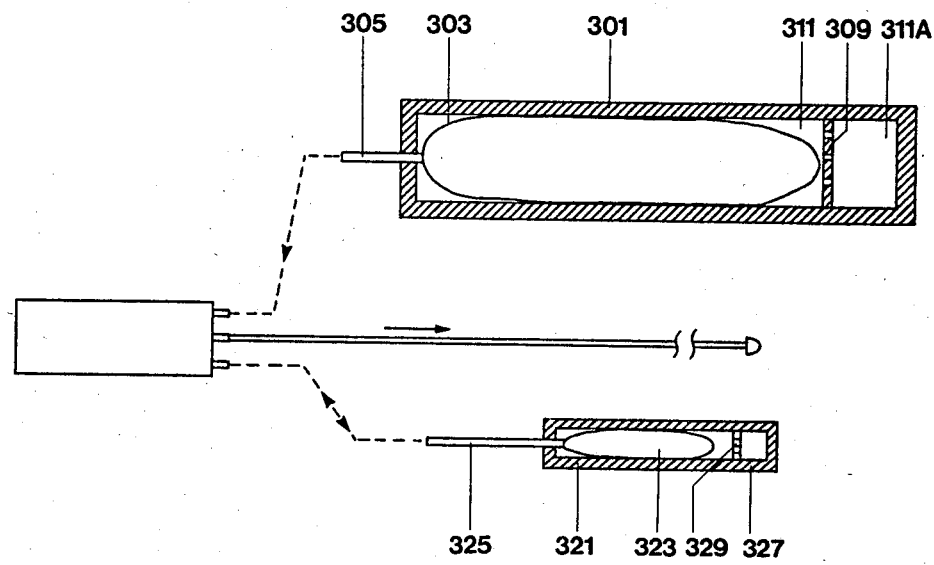
FIG. 14 is a schematic side elevation of two liquid containers used in a third embodiment of the invention.

FIG. 14 discloses a modification of the two liquid containers 1 and 7 used in the two previous embodiments. In this modification, the use of leaf springs to produce pressure in the liquid in the two containers is replaced by the use of substances such as propane, butane, FREON ® and other refrigerants which experience both a liquid phase and a vapour phase. At the ambient operating temperature of the device. It will be appreciated that this embodiment may be operated externally of the patient or may be implanted within the patient.

In this embodiment, the first liquid container 1 is replaced with a container 301 comprising a flexible envelope 303 having an outlet pipe 305 corresponding to pipe 17. Enclosing envelope 303 in a fluid-tight manner is a rigid casing 301. An optional perforated partition 309 prevents envelope 303 from encroaching on an end part 311A of the space 311 inside the casing 301 but outside envelope 303. Space 311 contains propane partly in the vapour phase at the ambient temperature. The propane will pressurize the envelope 303 to a pressure which depends on its temperature, despite changes in the volume of the envelope 303 as it empties. It is of course important that at all times some propane exists in its liquid phase.

The second container 321 corresponds to the container 7 and similarly comprises a flexible envelope 323 with an inlet/outlet pipe 325 corresponding to pipe 21. Container 301 includes a rigid casing 327 provided with a perforated partition 329. In this case, butane is used in casing 327 to pressurize the envelope 323.

It will be appreciated that, at normal room or body temperatures, the vapour pressure exerted by the butane is less than the vapour pressure exerted by the propane. So that the pressure in container 301 is sufficient to charge container 321. While the somewhat lesser pressure in container 321 is still sufficient to effect an injection into the patient.

The container 321 is so dimensioned that its walls act as stop means to limit the quantity of liquid which can be stored in container 321. This controls the amount of liquid injected at each pulse.

SUPPLEMENTARY DISCUSSION OF THE INVENTION

By the use of a first liquid storage container in which the liquid to be injected is stored at a pressure greater than that required for making injections, together with the use of a second liquid metering container which operates at a pressure lower than that in the first container but still higher than that required to make injections, the need for any power operated injection pump is avoided. Such pumps tend to be relatively fragile, and what is more important they required considerable power for their operation. The provision of a battery to supply such power is one of the reasons why other pulsatile devices are bulky and heavy. The battery of the present device needs only drive a small timing device, of negligible power consumption, and once every 2 hours supply an appreciable operating current for the solenoid coil 73. Although this current is appreciable, it is required only for a period of 5 seconds every 2 hours. A small battery can easily meet this demand for several days.

As a result of the absence of any motors and gearboxes, the whole apparatus is extremely inexpensive to produce compared with existing pulsatile devices. This permits the economic replacement of the whole package (with the exception of the belt or brassiere, the catheter or other injection needle, the electrical timer and a rechargeable battery) rather than its refilling by the patient. It is visualized that in practice such a package could be returnable as a discount against the cost of a replacement package. This also eliminates the risk of contamination and possible infection when a patient refills a container under non-sterile conditions.

We claim:

1. A pulsed liquid injection device comprising a first liquid storage container adapted to store liquid under pressure greater than that required for making injections, a second liquid metering container also adapted to store liquid under a pressure greater than that required for making injections and having a predetermined capacity for liquid at the pressure in the first container, valve means having first, second and third ports and having a first operating condition in which the valve means connect together the first and second ports but blank off the third port, and a second operating condition in which the valve means blank off the first port but connect together the second and third ports, first liquid flow passages connecting the first port to the interior of the first storage container, second fluid flow passages connecting the second port to the interior of the second metering container, a liquid dispensing duct connected to said third port and electrical timing means arranged repeatedly at predetermined intervals to apply an electrical operating pulse to the said valve means to change them from one initial operating condition to the other and, after a delay determined by the pulse length, to permit the valve means to return to their initial position.

2. A pulsed liquid injection device as claimed in claim 1, in which the electrical operating pulses cause the valve means to change from their first operating condition to their second operating condition.

3. A pulsed liquid injection device as claimed in claim 1, in which the first liquid storage container has flexible walls and spring means act on the exterior of said flexible walls in such a manner as to produce in said liquid a pressure greater than that required for making injections.

4. A pulsed liquid injection device as claimed in claim 3, in which said spring means consist of two leaf springs acting respectively on opposite walls of the container.

5. A pulsed liquid injection device as claimed in claim 1, in which the second liquid metering container has flexible walls and spring means act on the exterior of said flexible walls in such a manner as to provide the desired pressure and stop means limit the increase of the size of the container under internal pressure, so limiting the quantity of liquid which this container can accept.

6. A pulsed liquid injection device as claimed in claim 1, in which the valve means include a movable element, movable between a first operating position in which the valve means connect together the first and second ports but blank off the third port, and a second operating position in which the valve means blank off the first port but connect together the second and third ports.

7. A pulsed liquid injection device as claimed in claim 1, in which the said liquid is a medication, and including a waist belt provided with pockets into which are fitted the first storage container, the second metering container, the valve means, the electrical timing means and an operating battery.

8. A pulsed liquid injection device as claimed in claim 7, in which the first storage container, the second metering container and the valve means are assembled inside a disposable cassette.

9. A pulsed liquid injection device as claimed in claim 1, in which the said liquid is a medication, and including a brassiere into the cups of which are fitted the first storage container, the second metering container, the valve means, the electrical timing means and an operating battery.

10. A pulsed liquid injection device as claimed in claim 9, in which the first storage container, the second metering container and the valve means are assembled inside a disposable cassette.

11. A pulsed liquid injection device as claimed in claim 1, in which the first liquid storage container has flexible walls and is disposed in a fluid tight chamber, the part of the chamber outside the container being filled with a substance having a liquid phase and a vapour phase, there being sufficient of the substance to ensure that in use there will always exist some of the substance in the liquid phase.

12. A pulsed liquid injection device as claimed in claim 1, in which the second liquid metering container has flexible walls and is disposed in a fluid tight chamber, the part of the chamber outside the container being filled with a substance having a liquid phase and a vapour phase, there being sufficient of the substance to ensure that in use there will always exist some of the substance in the liquid phase, the chamber having parts which limit the maximum size the container can achieve and so limit the quantity of liquid which this container can accept.

13. A pulsed liquid injection device as claimed in claim 11, in which said substance is propane, the second liquid metering container has flexible walls and is disposed in a fluid tight chamber, the part of this chamber outside the container being filled with butane, which has a liquid phase and a vapour phase, there being sufficient butane to ensure that in use there will always exist some of the butane in liquid phase, and this chamber having parts which limit the maximum size the second container can achieve and so limit the quantity of liquid which this container can accept.

14. A cassette adapted for addition to a pulsed liquid injection system, of which it then forms part, the cassette including in its package a first liquid storage container adapted to store liquid under pressure greater than that required for making injections, a second liquid metering container also adapted to store said liquid under a pressure greater than that required for making injections and having a predetermined capacity for liquid at the pressure in the first container, valve means having first, second and third ports and having a first operating condition in which the valve means connect together the first and second ports but blank off the third port, and a second operating condition in which the valve means blank off the first port but connect together the second and third ports, first liquid flow passages connecting the first port to the interior of the first storage container, second fluid flow passages connecting the second port to the interior of the second metering container, a liquid dispensing duct connected to said third port, and electrical operating means for the valve means adapted upon application of an electrical pulse to change the valve means from one initial operating condition to the other and, after a delay determined by the pulse length, to permit the valve means to return to their initial position.

15. A pulse liquid injection device as claimed in claim 11, in which the second liquid metering container has flexible walls and springmeans act on the exterior of said flexible walls in such a manner as to provide the desired pressure and stop means limit the increase of the size of the container under internal pressure, so limiting the quantity of liquid which this container can accept.

16. A pulsed liquid injection device as claimed in claim 12, in which the first liquid storage container has flexible walls and spring means act on the exterior of said flexible walls in such a manner as to produce in said liquid a pressure greater than that required for making injections.

17. A pulsed liquid injection device as claimed in claim 15 wherein said substance is selected from propane, butane and Freon.

18. A pulsed liquid injection device as claimed in claim 16 wherein said substance is selected from propane, butane and Freon.

* * * * *